United States Patent

Hanessian et al.

Patent Number: 6,063,816
Date of Patent: May 16, 2000

[54] HYDROXAMIC ACID COMPOUNDS

[75] Inventors: Stephen Hanessian, Beaconsfield, Canada; Ghanem Atassi, Saint Cloud, France; Gordon Tucker, Paris, France; Daniel-Henri Caignard, Le Peco, France; Pierre Renard, Le Chesnay, France

[73] Assignee: Adir et Compagnie, Courbevoie, France

[21] Appl. No.: 09/370,712

[22] Filed: Aug. 9, 1999

[30] Foreign Application Priority Data

Aug. 10, 1998 [FR] France .................................. 98 10237

[51] Int. Cl.[7] .......................... A01N 37/28; A01N 43/40; A01K 31/19; C07C 259/04; C07D 211/32

[52] U.S. Cl. ......................... 514/575; 514/327; 514/331; 514/351; 514/459; 546/235; 546/337; 549/419; 562/623

[58] Field of Search ..................... 514/327, 331, 514/351, 459, 575; 546/235, 337; 549/419; 562/623

[56] References Cited

U.S. PATENT DOCUMENTS

| | | | |
|---|---|---|---|
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |
| 5,646,167 | 7/1997 | MacPherson et al. | 514/357 |
| 5,817,822 | 10/1998 | Nantermet et al. | 546/194 |

OTHER PUBLICATIONS

Database CAPLUS on STN, Acc. No. 1998:498326, Broka et al., 'Preparation of N–sulfamoylpiperidine–2–hydroxamic acids and analogs as metalloproteinase inhibitors.' DE 19802350 (abstract), Jul. 30, 1998.

*Primary Examiner*—Gary Geist
*Assistant Examiner*—Brian J. Davis
*Attorney, Agent, or Firm*—The Firm of Gordon W. Hueschen

[57] ABSTRACT

A compound selected from those of formula (I):

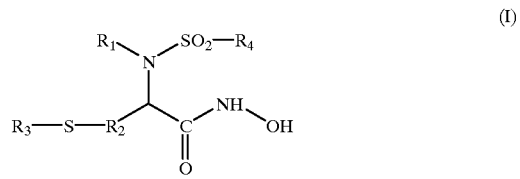

wherein:

$R_1$ represents optionally substituted alkyl, acyl, cycloalkyl, aryl, aminocarbonylalkyl, or heterocycle, $R_2$ represents alkylene, $R_3$ represents X or Y as defined in the description, $R_4$ represents—either alkyl, cycloalkyl, aryl, arylalkyl, cycloalkylalkyl, heterocycloalkylene, or heterocycle when $R_3$ represents Y, or biaryl, arylheteroaryl or heteroarylaryl, when $R_3$ represents X or Y, their isomers and also pharmaceutically-acceptable acid or base addition salts thereof, and medicinal products containing the same which are useful as metalloprotease inhibitors in the treatment of cancers.

14 Claims, No Drawings

HYDROXAMIC ACID COMPOUNDS

FIELD OF THE INVENTION

The present invention relates to new hydroxamic acid compounds. These new compounds are new metalloprotease inhibitors.

DESCRIPTION OF THE PRIOR ART

The restructuring of the extracellular matrix is involved in numerous physiological and pathological processes: embryonic development, cicatrisation, normal and pathological angiogenesis, degeneration of connective and articular tissue, invasive and metastatic cancers, for example.

The metalloproteinases of the extracellular matrix ('matrix metalloproteinases' or MMPs), enzymes described initially as being involved in regulating the formation and destruction of extracellular material, are over-expressed during the course of such events and are associated with pathological progression. This family of zinc proteases has at least fourteen members. The principal members for which the substrates are known are: the collagenases (interstitial MMP-1, neutrophilic MMP-8 and collagenase-3 or MMP-13), the gelatinases (type IV collagenases MMP-2 and MMP-9, or gelatinases A and B), metalloelastase MMP-12, the stromeylsins (including stromelysin-1 or MMP-3) and the gelatinase A activators (MT-MMPs, the only MMPs having a transmembrane domain).

In tumour pathology, those enzymes, secreted by the cancerous cells and the normal cells of the peritumoural stroma, take part directly in opening migration pathways in the interstitial tissue for the endothelial and tumour cells, and indirectly in the release and the maturation of membrane factors or sequestered factors in the extracellular matrix (angiogenesis or growth factors, inflammation mediators, such as α tumour necrosis factor or α-TNF . . . ), thus contributing to all stages of tumour progression (growth of the primary tumour, angiogenesis, local invasion and establishment of metastases).

MMP inhibitors would thus be especially effective as new pharmacological entities capable of curbing the progression of a large number of pathologies, including cancer.

Various metalloprotease inhibitors have been described in the literature, including, especially, the compounds described in the patent applications EP 606 046, WO 96/40101, WO 96/00214 and WO 97/27174 and also in the article J. Med. Chem., 1998, 41, 640–649.

Apart from the fact that the compounds of the present invention are new, they have proved to be more powerful metalloprotease inhibitors than those described in the literature, hence making them potentially useful in the treatment of cancers, rheumatic diseases such as arthrosis and rheumatoid arthritis, etc.

DETAIL DESCRIPTION OF THE INVENTION

More specifically, the present invention relates to compounds of formula (I):

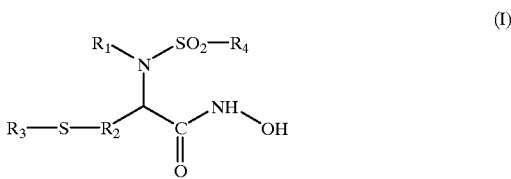

wherein:
$R_1$ represents:
a linear or branched ($C_1$–$C_6$)alkyl group (optionally substituted by one or more identical or different groups each selected independently of the other(s) from hydroxy, halogen, linear or branched ($C_1$–$C_6$)alkoxy, mercapto, linear or branched ($C_1$–$C_6$)alkylthio, aryl, linear or branched ($C_1$–$C_6$)acyl, and amino, which is itself optionally substituted by one or two identical or different linear or branched ($C_1$–$C_6$)alkyl groups, cycloalkyl groups or aryl groups),
a linear or branched ($C_1$–$C_6$)acyl group,
a cycloalkyl group,
an aryl group,
a heterocycle,
an aminocarbonyl-($C_1$–$C_4$)alkyl group, the amino moiety being optionally substituted by a linear or branched ($C_1$–$C_6$)alkyl group, the said ($C_1$–$C_6$) alkyl group being optionally substituted by one or more identical or different groups selected from aryl, aryl-$C_1$–$C_6$)alkyl in which the alkyl moiety may be linear or branched, cycloalkyl and linear or branched ($C_1$–$C_6$) alkylaminocarbonyl,
$R_2$ represents a linear or branched ($C_1$–$C_4$)alkylene group,
$R_3$ represents a group X or Y wherein:
X represents a linear or branched ($C_1$–$C_6$)alkyl group, a linear or branched ($C_1$–$C_6$)acyl group, a linear or branched ($C_1$–$C_6$)alkoxycarbonyl group, a linear or branched amino-($C_1$–$C_6$)alkyl group (the amino moiety itself being optionally substituted by one or two identical or different linear or branched ($C_1$–$C_6$)alkyl groups), a linear or branched hydroxy-($C_1$–$C_6$)alkyl group, a linear or branched carboxy-($C_1$–$C_6$)alkyl group, a linear or branched aminocarbonyl-($C_1$–$C_6$) alkyl group, a linear or branched mercapto-($C_1$–$C_6$) alkyl group, a cycloalkyl group, an aryl group or a heterocycle, and
Y represents a group of formula T-U-V- (the moiety V being bonded to the sulphur atom), in which:
T represents an aryl group or a heterocycle,
U represents a single bond, a sulphur atom, an oxygen atom, an NH or C=O group, or a group of formula —$R_8$O—, —$R_8$S—, —$R_8$NH—, —$R_8$OR_9$—, —$R_8$SR_9$—, —$R_8$NH—$R_9$—, —$R_8$—CO—$R_9$— or —$R_9$— in which $R_8$ represents a linear or branched ($C_1$–$C_6$)alkylene group and $R_9$ represents an arylene or heteroarylene group, it being understood that in those groups $R_8$ is bonded to the T moiety of the group Y and $R_9$ or the hetero atom is bonded to the V moiety of the group Y,
V represents a linear or branched ($C_1$–$C_6$)alkylene group,
$R_4$ represents:
either, when $R_3$ represents a group Y, a group selected from linear or branched ($C_1$–$C_6$)alkyl, cycloalkyl, aryl, aryl-($C_1$–$C_6$)alkyl in which the alkyl moiety may be linear or branched, cycloalkyl-($C_1$–$C_6$)alkyl in which the alkyl moiety may be linear or branched, linear or branched ($C_1$–$C_6$)alkyl substituted by a heterocycle, and a heterocycle, or, when $R_3$ represents a group X or Y, a group selected from biaryl, arylheteroaryl, and heteroarylaryl, to isomers thereof and also addition salts thereof with a pharmaceutically acceptable acid or base.

It will be understood that:

"cycloalkyl" is to be understood as being a mono- or bi-cyclic system from 3 to 10 carbon atoms, "aryl" is to be understood as being a phenyl, naphthyl tetrahydronaphthyl, dihydronaphthyl, indene or dihydroindene group, each of which is optionally substituted by one or more identical or different substituents selected from halogen, hydroxy, cyano, nitro, linear or branched ($C_1$–$C_6$)alkyl, linear or branched ($C_1$–$C_6$)trihaloalkyl, linear or branched ($C_1$–$C_6$)alkoxy, linear or branched ($C_1$–$C_6$)acyl, carboxy, linear or branched ($C_1$–$C_6$)alkoxycarbonyl and amino, amino itself being optionally substituted by one or two identical or different, linear or branched ($C_1$–$C_6$)alkyl groups, "biaryl" is to be understood as being an aryl group in which one of the carbon atoms of the ring is substituted by a second aryl group, "heterocycle" is to be understood as being a saturated or unsaturated mono- or bi-cyclic group having from 4 to 12 ring members and containing one, two or three identical or different hetero atoms selected from oxygen, nitrogen and sulphur, it being understood that the heterocycle may be optionally substituted by one or more identical or different substituents selected from halogen, hydroxy, linear or branched ($C_1$–$C_6$)alkyl, linear or branched ($C_1$–$C_6$)trihaloalkyl, linear or branched ($C_1$–$C_6$)alkoxy and amino, amino being optionally substituted by one or more linear or branched ($C_1$–$C_6$)alkyl groups, "heteroaryl" is to be understood as meaning as unsaturated heterocycle of aromatic character.

Advantageously, preferred compounds of the invention are those in which $R_1$ represents a linear or branched ($C_1$–$C_6$)alkyl group, and more particularly an isobutyl group.

According to one advantageous variant of the invention, preferred compounds are those in which $R_3$ represents a group X as defined hereinbefore and $R_4$ represents a biaryl, arylheteroaryl or heteroarylaryl group.

According to another advantageous variant of the invention, preferred compounds are those in which $R_3$ represents a group Y as defined hereinbefore and $R_4$ represents a linear or branched ($C_1$–$C_6$)alkyl group, a cycloalkyl group, an aryl group, an aryl-($C_1$–$C_6$)alkyl group in which the alkyl moiety may be linear or branched, a cycloalkyl-($C_1$–$C_6$)alkyl group in which the alkyl moiety may be linear or branched, a linear or branched ($C_1$–$C_6$)alkyl group substituted by a heterocycle, or a heterocycle.

According to a third especially advantageous variant, preferred compounds of the invention are those in which $R_3$ represents a group Y as defined hereinbefore and $R_4$ represents a biaryl, arylheteroaryl or heteroarylaryl group.

The preferred compounds according to the invention are:
4-(benzylsulfanyl)-2-{isobutyl-[(4-methoxyphenyl) sulphonyl]amino}butanehydroxyamic acid,
4-{[4-(phenyl)-benzyl]sulphanyl}-2-{isobutyl-[(4-methoxyphenyl)sulphonyl]amino}butanehydroxyamic acid,
4-{[4-(benzyloxy)benzyl]sulphanyl}-2-{isobutyl-[(4-methoxyphenyl)sulphonyl]amino}butanehydroxyamic acid,
2-{isobutyl[(4-biphenyl)sulphonyl)amino}-4-(methylsulphanyl)butanehydroxyamic acid,
4-(benzylsulphanyl)-2-{isobutyl-[(4-biphenyl)sulphonyl] amino}butanehydroxyamic acid,
and
2-{[2-(benzhydrylamino)-2-oxoethyl]-[(4-methoxyphenyl) sulphonyl]amino}-4-(benzylsulphanyl) butanehydroxyamic acid.

The isomers, and also the addition salts with a pharmaceutically acceptable acid or base, of the preferred compounds are an integral part of the invention.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

The invention extends also to a process for the preparation of the compounds of formula (I), which is characterised in that there is used as starting material a compound of formula (II):

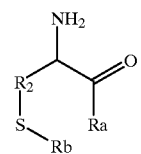

(II)

wherein $R_2$ is as defined for formula (I) and either Ra and Rb form a single bond connecting the carbonyl group to the sulphur atom, or Ra represents linear or branched ($C_1$–$C_6$) alkoxy group and Rb represents a linear or branched ($C_1$–$C_6$)alkyl group, the primary amine function of which compounds of formula (II) is substituted, according to conventional conditions of organic synthesis, by a compound of formula (II'):

(II')

wherein $R_1$ is as defined for formula (I) and Z represents a leaving group customary in organic chemistry, to yield the compounds of formula (III)

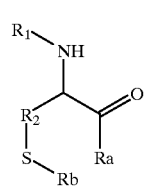

(III)

wherein $R_1$ and $R_2$ are as defined for formula (I) and Ra and Rb are as defined hereinbefore, which compounds of formula (III) are treated under basic conditions with a compound of formula (IV):

wherein $R_4$ is as defined for formula (I),
to yield the compounds of formula (V),

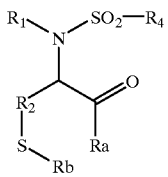

wherein $R_1$, $R_2$, $R_4$, and Ra and Rb are as defined hereinbefore,
which compounds of formula (V), when Ra and Rb form a single bond, are treated in the presence of methanol and sodium with a compound of formula (VI):

wherein $R_3$ is as defined for formula (I) and Hal represents a halogen atom, to yield the compounds of formula (VII):

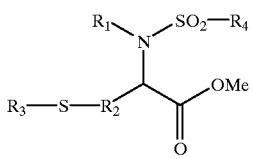

wherein $R_1$, $R_2$, $R_3$ and $R_4$ are as defined for formula (I), the totality of the compounds of formulae (VII) and (V) constituting the compounds of formula (IX):

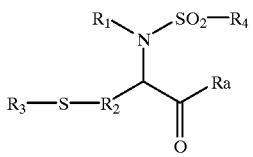

wherein $R_1$, $R_2$, $R_3$, and $R_4$ and Ra are as defined hereinbefore,
the ester function of which compounds of formula (IX) is hydrolysed according to conventional conditions to yield the compounds of formula (X):

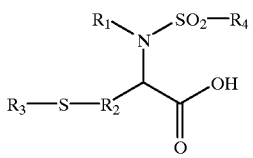

wherein $R_1$, $R_2$, $R_3$ and $R_4$ are as defined hereinbefore,
which compounds of formula (X) are treated either directly with hydroxylamine hydrochloride, or with an O-substituted hydroxylamine which is deprotected subsequently according to conventional operating conditions, to yield the compounds of formula (I) as defined hereinbefore,
which compound of formula (I) is, if necessary, purified according to a conventional purification technique, is optionally separated into its isomers according to a conventional separation technique and is, if desired, converted into an addition salt thereof with a pharmaceutically acceptable acid or base.

The compounds of formulae (II), (II'), (IV) and (VI) are either commercially available compounds, or are obtained according to conventional methods of organic synthesis.

The present invention relates also to pharmaceutical compositions comprising as active ingredient at least one compound of formula (I), an optical isomer thereof or an addition salt thereof with a pharmaceutically acceptable acid or base, alone or in combination with one or more inert, non-toxic, and pharmaceutically acceptable excipients or carriers.

Among the pharmaceutical compositions according to the invention there may be mentioned more especially those which are suitable for oral, parenteral (intravenous, intramuscular or subcutaneous), per- or trans-cutaneous, nasal, rectal, perlingual, ocular or respiratory administration, and especially tablets or dragées, sublingual tablets, soft gelatin capsules, hard gelatin capsules, suppositories, creams, ointments, dermal gels, injectable or drinkable preparations, aerosols, eye or nose drops, etc.

The dosage used varies according to the age and weight of the patient, the administration route, the nature and severity of the disorder and the administration of possible associated treatments, and ranges from 1 to 500 mg in one or more administrations per day.

The following Examples illustrate the invention but do not limit it in any way.

The starting materials used are known products or are prepared according to known procedures.

The various synthesis steps yield synthesis intermediates that are useful in the preparation of the compounds of the invention.

The structures of the compounds described in the Examples and in the synthesis steps have been determined according to customary spectrophotometric techniques (infra-red, NMR, mass spectrometry . . . ).

EXAMPLE 1

4-(Benzylsulfanyl)-2-{isobutyl-[(4-methoxyphenyl) sulphonyl]amino}butanehydroxyamic acid Step A: 3-(Isobutylamino)tetrahydro-2-thiophenone 4.6 mmol of triethylamine are added at 0° C., under an inert atmosphere, to a solution of 4.23 mmol of D-homocysteine thiolactone hydrochloride and 8.46 mmol of isobutyraldehyde in 20 ml of methanol. After stirring for 4 hours at ambient temperature, the reaction mixture is cooled to 0° C. and 8.8 mmol of NaCNBH$_3$ are slowly added in the course of 40 minutes. After stirring for 30 minutes at 0° C., the reaction mixture is hydrolysed and then extracted with ether. The combined organic phases are then washed with a saturated NaCl solution, dried over sodium sulphate, filtered and concentrated under reduced pressure. Chromatography on silica gel (dichloromethane/methanol: 99/1) allows the expected product to be isolated in the form of syrup.

Step B: N1-Isobutyl-N1-(2-oxotetrahydro-3-thiophenyl)-4-methoxy-1-benzensulphonamide 5 mmol of N-methylmorpholine and 2.5 mmol of 4-methoxyphenylsulphonyl chloride are added at 0° C. to a solution of 2.5 mmol of the compound obtained in Step A in 15 ml of dichloromethane. After stirring for 12 hours at ambient temperature, the reaction mixture is poured into water and then extracted with dichloromethane. The combined organic phases are washed with a 2N hydrochloric acid solution, then with a 5% solution of NaHCO$_3$, and then with water. After drying over sodium sulphate, filtration and evaporation, chromatography on silica gel (dichloromethane/methanol: 20/1) allows the expected product to be isolated.

Melting point: 92° C.

Step C: Methyl 4-(benzylsulphanyl)-2-{isobutyl-[(4-methoxyphenyl)sulphonyl]amino}butanoate 1.1 mmol of the compound obtained in Step B are added at ambient temperature to a solution of 1.26 mmol of sodium in 3 ml of methanol. After stirring for 15 minutes, 1.1 mmol of benzyl bromide are added and stirring is maintained for two hours. After evaporation of the methanol, a solid is obtained with is triturated in ethyl acetate and filtered. Evaporation of the filtrate allows a residue to be obtained, which is purified by chromatography on silica gel (dichloromethane/methanol: 20/1), allowing the expected product to be isolated in the form of syrup.

Mass spectrum: FAB$^+$:[M$^+$+1]:m/z=466

Step D: 4-(Benzylsulfanyl)-2-{isobutyl-[(4-methoxyphenyl)sulphonyl]amino}butanoic acid 1.77 mmol of potassium hydroxide are added to 0.95 mmol of the compound obtained in Step C in a 3/1 mixture of dioxane/water. After stirring for 3 hours at 50° C., the dioxane is evaporated off, the residual aqueous phase is diluted with water, acidified to pH 2 by the addition of a 5% hydrochloric acid solution, and then extracted with ethyl acetate. The combined organic phases are washed, dried and filtered and then evaporated under reduced pressure. Chromatography on silica gel (dichloromethane/methanol: 93/7) allows the expected product to be isolated in the form of syrup.

Step E: N-tert-Butoxy-4-benzylsulphanyl-2-{isobutyl-[(4-methoxyphenyl)sulphonyl]amino}butanamide 0.6 mmol of the compound obtained in Step D, 0.6 mmol of 1-hydroxybenzotriazole, 3 mmol of N-methylmorpholine and 1.2 mmol of O-tert-butylhydroxylamine hydroxchloride are dissolved in 9 ml of dichloromethane. 0.78 mmol of N-[(dimethylamino)propyl]-N-ethylcarbodiimide hydrochloride is then added to that solution and the reaction mixture is stirred at ambient temperature for 12 hours. The reaction mixture is then diluted by adding water and is subsequently extracted with dichloromethane. The combined organic phases are washed with a saturated NaCl solution, dried over sodium sulphate, filtered and concentrated under reduced pressure. Chromatography on silica gel (dichloromethane/methanol: 99/1) allows the product to be isolated in the form of syrup.

Mass spectrum: FAB$^+$:(M$^+$+1):m/z=523

Step F: 4-(Benzylsulphanyl)-2-{isobutyl-[(4-methoxyphenyl)sulphonyl]amino}butanehydroxamic acid A solution containing 0.31 mmol of the compound obtained in Step E in 2 ml of dichloromethane and 2 ml of trifluoroacetic acid is stirred for 6 hours at ambient temperature, then concentrated under reduced pressure and subjected to chromatography on silica gel (dichloromethane/methane: 98/2). A syrupy residue is obtained, which is then dissolved in ethyl acetate. The solution is subsequently filtered over Celite and then concentrated under reduced pressure, allowing the expected product to be isolated in the form of syrup.

Mass spectrum: FAB$^+$:(M$^+$+1):m/z=467 (M$^+$-CONHOH):m/z=406

EXAMPLE 2

4-{[4-(Phenyl)benzyl]sulphanyl}-2-{isobutyl-[(4-methoxyphenyl)sulphonyl]amino}butanehydroxamic acid The product is obtained in accordance with the process described in Example 1, using 4-(phenyl)benzyl bromide as the reagent in Step C.

Step C: Methyl 4-{[4-(phenyl)benzyl]sulphanyl}-2-{isobutyl-[(4-methoxyphenyl)sulphonyl]amino}butanoate
Step D: 4-{[4-(Phenyl)benzyl]sulphanyl}-2-{isobutyl-[(4-methoxyphenyl)sulphonyl]amino}butanoic acid
Step E: N-tert-Butoxy-4-{[4-(phenyl)benzyl]sulphanyl}-2-{isobutyl-[(4-methoxyphenyl)sulphonyl]amino}butanamide
Step F: 4-{[4-(Phenyl)benzyl]sulphanyl}-2-{isobutyl-[(4-methoxyphenyl)sulphonyl]amino}butanehydroxamic acid

EXAMPLE 3

4-(Benzylsulfanyl)-2-{isobutyl-[(4-biphenyl)sulphonyl]amino}butanehydroxyamic acid The product is obtained in accordance with the process described in Example 1, using 4-biphenylsulphonyl chloride as the reagent in Step B.

Step B: N1-Isobutyl-N1-(2-oxotetrahydro-3-thiophenyl)-4-phenyl-1-benzenesulphonamide
Step C: Methyl 4-(benzylsulphanyl)-2-{isobutyl-[(4-biphenyl)sulphonyl]amino}butanoate
Step D: 4-(Benzylsulphanyl)-2-{isobutyl-[(4-biphenyl)sulphonyl]amino}butanoic acid
Step E: N-tert-Butoxy-4-(benzylsulphanyl)-2-{isobutyl-[(4-biphenyl)sulphonyl]amino}butanamide
Step F: 4-(Benzylsulphanyl)-2-{isobutyl-(4-biphenyl)sulphonyl]amino}butanehydroxamic acid

EXAMPLE 4

4-{[4-(Benzyloxy)benzyl]sulphanyl}-2-{isobutyl-[(4-methoxyphenyl)sulphonyl]amino}butanehydroxamic acid The product is obtained in accordance with the process descried in Example 1, Steps A to D, using as the reagent in Step C 4-(benzyloxy)benzyl bromide, and then carrying out Step G described hereinbelow.

Step C: Methyl 4-{[4-(benzyloxy)benzyl]sulphanyl}-2-{isobutyl-[(4-methoxyphenyl)sulphonyl]amino}butanoate
Step D: 4-{[4-(Benzyloxy)benzyl]sulphanyl}-2-{isobutyl-[(4-methoxyphenyl)sulphonyl]amino}butanoic acid
Step G: 4-{[4-(Benzyloxy)benzyl]sulphanyl}-2-{isobutyl-[(4-methoxyphenyl)sulphonyl]amino}butanehydroxamic acid 1 mmol of the compound obtained in Step D, 1 mmol of 1-hydroxybenzotriazole, 5 mmol of N-methylmorpholine and 2 mmol of hydroxylamine hydrochloride are dissolved in 15 ml of dichloromethane. 1.2 mmol of N-[(dimethylamino)propyl]-N-ethylcarbodiimide hydrochloride are then added to that solution and the reaction mixture is stirred at ambient temperature for 12 hours. The reaction mixture is then hydrolysed by the addition of water, and the aqueous phase is subsequently extracted with dichloromethane. The combined organic phases are washed with a saturated NaCl solution, dried over sodium sulphate, filtered and concentrated under reduced pressure. Chromatography on silica gel (dichloromethane/methanol: 98/2) allows the expected product to be isolated.

EXAMPLE 5

2-{Isobutyl[(4-biphenyl)sulphonyl)]amino}-4-(methylsulphanyl)butanehydroxyamic acid Step H: Methyl 2-amino-4-methylsulphanyl)butanoate hydrochloride There are added to 15 ml of methanol, at −10° C., 16.5 mmol of thionyl chloride and then, in small fractions, 11 mmol of D-methionine. Once the addition is complete, the reaction mixture is brought to ambient temperature. After 12 hours, the reaction mixture is concentrated under reduced pressure to yield crystals, which are recrystallised from an ether/methanol mixture, allowing the expected product to be isolated.

Melting point: 143° C.

Step I: Methyl 2-(isobutylamino)-4-(methylsulphanyl) butanoate 4.3 mmol of triethylamine are added at 0° C. and under an inert atmosphere to a solution of 3.9 mmol of the compound obtained in Step H and 7.8 mmol of isobutyraldehyde in 20 ml of methanol. After reaction for 6 hours at ambient temperature, the reaction mixture is cooled to 0° C. and 7.8 mmol of $NaBH_4$ are added over a period of 40 minutes. When the addition is complete, stirring is maintained for 30 minutes at 0° C., and the reaction mixture is then hydrolysed by the addition of an aqueous $NaHCO_3$ solution. After extraction with ether, the combined organic phases are washed with a saturated NaCl solution, dried over sodium sulphate and then concentrated under reduced pressure. Chromatography on silica gel (dichloromethane/methane: 99/1) allows the expected product to be isolated.

Step J: Methyl 2-{isobutyl-[(4-phenyl)phenylsulphonyl]amino}-4-(methylsulphanyl)butanoate 3.71 mmol of triethylamine and 1.8 mmol of 4-biphenylsulphonyl chloride are added at 0° C. to a solution of 1.8 mmol of the compound obtained in Step I in 15 ml of dichloromethane. The reaction mixture is brought to ambient temperature and stirred for 12 hours, and then poured into water and extracted with dichloromethane. The combined organic phases are washed with a 2N hydrochloric acid solution and then with an $NaHCO_3$ solution, dried, filtered, and concentrated under reduced pressure. Chromatography on silica gel (dichloromethane/methanol: 20/1) allows the expected product to be isolated in the form of syrup.

Step K: 2-{Isobutyl-[4-(biphenyl)sulphonyl]amino}-4-(methylsulphanyl)butanehydroxamic acid The product obtained in Step J is subjected to the procedure described in Example 1, Step D to Step F, allowing the expected product to be obtained.

Mass spectrum: $FAB^+$:(M$^+$+1):m/z=437; [M$^+$-CONHOH]: m/z=376

EXAMPLE 6

2-{[2-Benzhydrylamino)-2-oxoethyl]-[(4-methoxyphenyl)sulphonyl]amino}-4-(benzylsulphanyl)butanehydroxamic acid Preparation 1: tert-Butyl 2-[(2-oxotetrahydro-3-thiophenyl)amino]acetate 5.5 mmol of diisopropylethylamine and then 5.5 mmol of tert-butyl bromoacetate are added at 0° C. to a solution of 5 mmol of thiolactone in 10 ml of acetonitrile. After stirring for 30 minutes, the reaction mixture is brought to ambient temperature for 12 hours. The reaction mixture is concentrated under reduced pressure and subsequently subjected to chromatography on silica gel (dichloromethane/methanol: 97/3) allowing the expected product to be isolated.

Step B: tert-Butyl 2-{[(4-methoxyphenyl)sulphonyl]-(2-oxotetrahydro-3-thiophenyl)amino}acetate The procedure is as in Step B of Example 1, using as substrate the product obtained in Preparation 1.

Mass spectrum: $FAB^+$:[M$^+$+1]: m/z=402

Step C: Methyl 4-(benzylsulphanyl)-2-{[2-(tert-butoxy)-2-oxoethyl]-[(4-methoxyphenyl)sulphonyl]amino}butanoate The procedure is as in Step C in Example 1, using the product obtained in the above Step.

Mass Spectrum: $FAB^+$:[M$^+$+1]:m/z=524

Step L: 2-{[3-(Benzylsulphanyl)-1-(methoxycarbonyl)propyl]-[(4-methoxyphenyl)sulphonyl]amino}acetic acid A solution of 0.8 mmol of the compound obtained in Step C in 2 of dichloromethane and 3 ml of trifluoroacetic acid is stirred for 2 hours at ambient temperature. The reaction mixture is then concentrated under reduced pressure, and the residue is subsequently subjected to chromatography on silica gel (dichloromethane/methanol: 95/5) allowing the expected product to be isolated.

Mass spectrum: $FAB^+$:[M$^+$+1]:m/z=468

Step M: Methyl 2-{[2-benzhydrylamino)-2-oxoethyl]-[(4-methoxyphenyl)sulphonyl]amino}-4-(benzylsulphanyl)butanoate 1.8 mmol of benzotriaol-1-yloxytris(dimethylamino)phosphonium hexafluorophosphate and then 3 mmol of diisopropylethylamine are added at 0° C. to a solution of 1.5 mmol of the compound obtained in Step L and 1.6 mmol of aminodiphenylmethane in 20 ml of acetonitrile. The reaction mixture is then slowly brought to ambient temperature. After reaction for 6 hours, the acetonitrile is evaporated off and the residue is taken up in ethyl acetate and then washed with a saturated NaCl solution. The organic phases are dried over sodium sulphate, filtered and then concentrated under reduced pressure. Chromatography on silica gel (dichloromethane/methanol: 20:1) allows the expected product to be isolated.

Mass spectrum: $FAB^+$:[M$^+$+1]:m/z=633

Step N: 2-{[2-(Benzhydrylamino)-2-oxoethyl]-[(4-methoxyphenyl)sulphonyl]amino}-4-(benzylsulphanyl)butanehydroxamic acid The procedure is as in Example 1, Steps D to F, using the product obtained in the above Step M as substrate.

Mass spectrum: $FAB^+$:[M$^+$+1]:m/z=634

EXAMPLE 7

2-{[2-Benzhydrylamino)-2-oxoethyl]-[(4-biphenyl)sulphonyl]amino}-4-(benzylsulphanyl)butanehydroxamic acid The product is obtained in accordance with the process described in Example 6, using 4-biphenylsulphonyl chloride as the reagent in Step B.

EXAMPLE 8

4{[(1-Methyl-3-piperidyl)methyl]sulphanyl}-2-[isobutyl-(4-biphenylsulphonyl)amino]butanehydroxamic acid The product is obtained in accordance with the process described in Example 1, Steps A to F, using as the reagent in Step B that used in Example 3 and, as the reagent in Step C, 3-chloromethyl-1-methylpiperidine.

EXAMPLE 9

4-[(1-Naphthylmethyl)sulphanyl]-2-{isobutyl-[(4-methoxyphenyl)-sulphonyl]amino}butanehydroxamic acid The product is obtained in accordance with the process described in Example 1, Steps A to F, using 1-(chloromethyl)naphthalene as the reagent in Step C.

EXAMPLE 10

4-{[(Phenylsulphanyl)methyl]sulphanyl]}-2-[isobutyl-(4-biphenylsulphonyl)amino]butanehydroxyamic acid The product is obtained in accordance with the process described in Example 1, Steps A to F, using as the reagent in Step B that used in Example 3 and, as the reagent in Step C, methylthiophenyl chloride.

EXAMPLE 11

4-[(3-Pyridylmethyl)sulphanyl]-2-[isobutyl-(4-biphenylsulphonyl)amino]butanehydroxamic acid The product is obtained in accordance with the process described in Example 1, Steps A to F, using as the reagent in Step B that used in Example 3 and, as the reagent in Step C, 3-chloromethylpyridine.

EXAMPLE 12

4-{[2-(Tetrahydro-2H-pyranyl)methyl]sulphanyl}-2-{isobutyl-[4-(methoxyphenyl)sulphonyl]amino}butanehydroxamic acid The product is obtained in accordance with the process described in Example 1, Steps A to F, using 2-(chloromethyl)-tetrahydro-2H-pyran as the reagent in Step C.

EXAMPLE 13

4-[(Phenylsulphanylethyl)sulphanyl]-2-{isobutyl-[4-(methoxyphenyl)sulphonyl]amino}butanehydroxamic acid The product is obtained in accordance with the process described in Example 1, Steps A to F, using ethylthiophenyl chloride as the reagent in Step C.

PHARMACOLOGICAL STUDY OF THE COMPOUNDS OF THE INVENTION

EXAMPLE 14

Enzymatic Inhibition of the Metalloproteases

The enzymatic screening tests of the compounds are carried out in solution on all or some of the following four purified human enzymes: interstitial collagenase MMP-1, gelatinases MMP-2 and MMP-9, stromelysin-1 MMP-3. The activity is demonstrated by a fluorometric method adapted to a 96-well plate format.
Activation of the MMPs The step enables conversion of the pro-forms of the metalloenzymes into activated forms capable of cleaving the substrates used. The commercial enzymes, in aliquot amounts and stored at −80° C., are diluted in a 50 mM Tris buffer, 200 mM NaCl, 5 mM $CaCl_2$, 0.1% Brij 35, pH 7.7 at concentrations of 355 μg/ml (MMP-1), 444 μg/ml (MMP-2), 187 μg/ml (MMP-3) and 500 μg/ml (MMP-9) of enzyme in the presence of 2 mM APMA (4-aminophenylmercuric acetate) at 37° C. for 30 minutes (MMP-2 and MMP-9) or 1 hour (MMP-1 and MMP-3).
Fluorogenic Test The principle is based on the appearance of fluorescence after cleavage of a peptide pseudo-substrate in the presence of the activated enzyme. The peptide Dnp-Pro-β-cyclohexyl-Ala-Gly-Cys(Me)-His-Ala-Lys(N-Me-Abz)-$NH_2$ (Bachem, Switzerland) is cleaved between the glycine and the cysteine (Anal. Biochem. 1993, 212, 58–64) by the activated enzymes MMP-1, MMP-2 and MMP-9. The peptide (7-methoxycoumarin-4-yl)-Arg-Pro-Lys-Pro-Tyr-Ala-Nva-Trp-Met-Lys(Dnp)-$NH_2$ (Bachem) is cleaved between Ala and Nva (Anal. Biochem. 1993, 212, 58–64) by the activated enzyme MMP-3 (Biochemistry 1992, 31, 12618–12623). The tests are carried out in 50 mM Tris buffer, 200 mM NaCl, 5 mM $CaCl_2$, 0.1% Brij 35, pH 7.7, containing the diluted purified enzymes (at the final concentrations: 1.25, 2, 1.25 and 1 μg/ml for the enzymes MMP-1, MMP-2, MMP-3 and MMP-9, respectively). After preincubation of the enzymes with or without the products being tested (minimum of five doses in dilutions of 10 in 10), the cleavage reactions are initiated by adding 20 μM (final concentration) of the appropriate peptide pseudosubstrate in a total final volume of 100 μl (96-well plate format). After incubation for six hours at 37° C. in a humid atmosphere, the plates containing the samples are read in a cytofluorimeter (Cytofluor 2350, Millipore PerSeptive Systems, France) fitted with a combination of excitation filters and emission filters of 340 and 440 nm, respectively. Each condition is carried out in triplicate. The concentration that inhibits 50% of the reaction ($IC_{50}$) is then determined from curves showing the intensity of the fluorescence of the cleavage products as a function of the amounts tested. Each experiments is carried out at least twice.

In the above test, the compounds of the invention exhibited $IC_{50}$ values of from 100 to 200 nM for the enzyme MMP-1, and from 0.2 to 50 nM for the enzymes MMP-2, MMP-3 and MMP-9.

EXAMPLE 15

Pharmaceutical Composition: Tablets

Formulation for the preparation of 1000 tablets each containing 20 mg of active ingredient compound of Example 2 . . . 20 g
hydroxypropyl cellulose . . . 2 g
wheat starch . . . 10 g
lactose . . . 100 g
magnesium stearate . . . 3 g
talc . . . 3 g

What is claimed is:

1. A compound selected from the group consisting of those of formula (I):

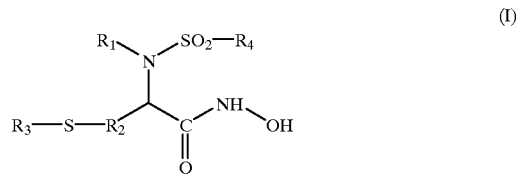

wherein:

$R_1$ represents a member selected from the group consisting of:

linear or branched ($C_1$–$C_6$)alkyl (optionally substituted by one or more identical or different groups each selected independently of the other(s) from hydroxy, halogen, linear or branched ($C_1$–$C_6$)alkoxy, mercapto, linear or branched ($C_1$–$C_6$)alkylthio, aryl, linear or branched ($C_1$–$C_6$)acyl, and amino, which is itself optionally substituted by one or two identical or different linear or branched ($C_1$–$C_6$)alkyl, cycloalkyl or aryl), linear or branched ($C_1$–$C_6$)acyl, cycloalkyl, aryl, heterocycle, and aminocarbonyl-($C_1$–$C_4$)alkyl, the amino moiety being optionally substituted by linear or branched ($C_1$–$C_6$)

alkyl, the said ($C_1$–$C_6$) alkyl being optionally substituted by one or more identical or different groups selected from aryl, aryl-$C_1$–$C_6$alkyl in which the alkyl moiety is linear or branched, cycloalkyl and linear or branched ($C_1$–$C_6$)alkylaminocarbonyl, $R_2$ represents a linear or branched ($C_1$–$C_4$)alkylene, $R_3$ represents a group X or Y wherein:

X represents a member selected from the group consisting of linear or branched ($C_1$–$C_6$)alkyl, a linear or branched ($C_1$–$C_6$)acyl, a linear or branched ($C_1$–$C_6$) alkoxycarbonyl, a linear or branched amino-($C_1$–$C_6$) alkyl (the amino moiety itself being optionally substituted by one or two identical or different linear or branched ($C_1$–$C_6$)alkyl), a linear or branched hydroxy-($C_1$–$C_6$)alkyl, linear or branched carboxy-($C_1$–$C_6$) alkyl, linear or branched aminocarbonyl-($C_1$–$C_6$)alkyl, linear or branched mercapto-($C_1$–$C_6$)alkyl, cycloalkyl, aryl, or a heterocycle, and Y represents a group of formula T-U-V- (the moiety V being bonded to the sulphur), in which:

T represents an aryl group or a heterocycle,

U represents a member selected from the group consisting of single bond, a sulphur, oxygen, NH C=O, a group of formula —$R_8$O—, —$R_8$S—, —$R_8$NH—, —$R_8$O$R_9$—, —$R_8$S$R_9$—, —$R_8$NH—$R_9$—, —$R_8$—CO—$R_9$— or —$R_9$— in which $R_8$ represents linear or branched ($C_1$–$C_6$)alkylene and $R_9$ represents an arylene or heteroarylene group, it being understood that in those groups $R_8$ is bonded to the T moiety of the group Y and $R_9$ or the hetero atom is bonded to the V moiety of the group Y, V represents linear or branched ($C_1$–$C_6$)alkylene, $R_4$ represents:

either, when $R_3$ represents a group Y, a group selected from linear or branched ($C_1$–$C_6$)alkyl, cycloalkyl, aryl, aryl-($C_1$–$C_6$)alkyl in which the alkyl moiety may be linear or branched, cycloalkyl-($C_1$–$C_6$)alkyl in which the alkyl moiety may be linear or branched, linear or branched ($C_1$–$C_6$)alkyl substituted by heterocycle, and heterocycle, or, when $R_3$ represents X or Y, a group selected from biaryl, arylheteroaryl, and heteroarylaryl, and an isomer and a pharmaceutically-acceptable acid or base addition salt thereof, it being understood that:

"cycloalkyl" means a mono- or bi-cyclic system having 3 to 10 carbons, inclusive, "aryl" means phenyl, naphthyl, tetrahydronaphthyl, dihydronaphthyl, indene or dihydroindene, each of which is optionally substituted by one or more identical or different substituents selected from halogen, hydroxy, cyano, nitro, linear or branched ($C_1$–$C_6$)alkyl, linear or branched ($C_1$–$C_6$)trihaloalkyl, linear or branched ($C_1$–$C_6$)alkoxy, linear or branched ($C_1$–$C_6$) acyl, carboxy, linear or branched ($C_1$–$C_6$) alkoxycarbonyl and amino, amino itself being optionally substituted by one or two identical or different, linear or branched ($C_1$–$C_6$)alkyl, "biaryl" means aryl in which one carbon of the ring is substituted by a second aryl, "heterocycle" means a saturated or unsaturated mono- or bi-cyclic group having 4 to 12 ring members and containing one, two or three identical or different hetero atoms selected from oxygen, nitrogen and sulphur, it being understood that heterocycle may be optionally substituted by one or more identical or different substituents selected from halogen, hydroxy, linear or branched ($C_1$–$C_6$)alkyl, linear or branched ($C_1$–$C_6$) trihaloalkyl, linear or branched ($C_1$–$C_6$)alkoxy and amino, amino being optionally substituted by one or more linear or branched ($C_1$–$C_6$)alkyl, and "heteroaryl" means an unsaturated heterocycle of aromatic character.

2. A compound of claim 1, wherein $R_3$ represents X as defined hereinbefore, and $R_4$ represents biaryl, arylheteroaryl or heteroarylaryl.

3. A compound of claim 1, wherein $R_3$ represents Y as defined hereinbefore and $R_4$ represents linear or branched ($C_1$–$C_6$)alkyl, cycloalkyl, aryl, aryl-($C_1$–$C_6$)alkyl in which the alkyl moiety is linear or branched, cycloalkyl-($C_1$–$C_6$) alkyl in which the alkyl moiety is linear or branched, linear or branched ($C_1$–$C_6$)alkyl substituted by heterocycle, or heterocycle.

4. A compound of claim 1, wherein $R_3$ represents Y and $R_4$ represents biaryl, arylheteroaryl, or heteroarylaryl.

5. A compound of claim 1, wherein $R_1$ represents linear or branched ($C_1$–$C_6$)alkyl.

6. A compound of claim 1, wherein $R_1$ represents isobutyl.

7. A compound of claim 1, which is 4-(benzylsulphanyl)-2-{isobutyl[(4-methoxyphenyl)sulphonyl] amino}butanehydroxyamic acid.

8. A compound of claim 1, which is 4-{[4-(phenyl)benzyl] sulphanyl}-2-{isobutyl-[(4-methoxyphenyl)sulphonyl] amino}butanehydroxamic acid.

9. A compound of claim 1, which is 4-(benzylsulphanyl)-2-{isobutyl[(4-biphenyl)sulphonyl] amino}butanehydroxamic acid.

10. A compound of claim 1, which is 4-{[4-(benzyloxy) benzyl]sulphanyl}-2-{isobutyl-[(4-methoxyphenyl) sulphonyl]amino}butanehydroxamic acid.

11. A compound of claim 1, which is 2-{isobutyl-[(4-biphenyl)sulphonyl]amino}-4-(methylsulphanyl) butanehydroxamic acid.

12. A compound of claim 1, which is 2-{[2-(benzhydrylamino)-2-oxoethyl]-[(4-methoxyphenyl) sulphonyl]amino}-4-(benzylsulphanyl)butanehydroxamic acid.

13. A method of treating a living body afflicted with a condition requiring a metalloprotease inhibitor comprising the step of administering to the living body an amount of a compound of claim 1 which is effective for alleviation of said condition.

14. A pharmaceutical composition useful as a metalloproteinase inhibitor for the treatment of invasive and metastatic cancers comprising as active principle an effective amount of a compound as claimed in claim 1, in combination with one or more pharmaceutically-acceptable excipients or carriers.

* * * * *

UNITED STATES PATENT AND TRADEMARK OFFICE
CERTIFICATE OF CORRECTION

PATENT NO. : 6,063,816
DATED : May 16, 2000
INVENTOR(S) : S. Hanessian, G. Atassi, G. Tucker, D-H. Caignard and P. Renard It is certified that error appears in the above-identified patent and that said Letters Patent is hereby corrected as shown below:

<u>Title page,</u>
Item [75] Inventors, Daniel-Henri Caignard, "Le Peco" should read -- Le Pecq --.

<u>Column 3,</u>
Line 11, insert the word -- having -- after the word "system".

<u>Column 4,</u>
Line 49, Formula (II') should read as follows:
-- $R_1 - Z$     (II') --

<u>Column 5,</u>
Lines 16 and 48, delete the word "and" (first instance).

<u>Column 10,</u>
Line 5, at the beginning of the line, "C in 2 of" should read -- C in 2ml of --.

<u>Column 12,</u>
Line 19, "experiments" should read -- experiment --.

<u>Column 13,</u>
Line 3, "aryl - $C_1$-$C_6$)" should read -- aryl - ($C_1$-$C_6$) --.
Line 24, insert a -- , -- (comma) after "NH".
Line 27, insert a -- , -- (comma) after "CO-$R_9$ -".

Signed and Sealed this

Fourth Day of June, 2002

*Attest:*

*Attesting Officer*

JAMES E. ROGAN
*Director of the United States Patent and Trademark Office*